United States Patent [19]

Molina

[11] 4,365,516

[45] Dec. 28, 1982

[54] ULTRASONIC COUPLANT GEL COMPOSITIONS AND METHOD FOR EMPLOYING SAME

[75] Inventor: Orlando G. Molina, Westminster, Calif.

[73] Assignee: Rockwell International Corporation, El Segundo, Calif.

[21] Appl. No.: 867,549

[22] Filed: Jan. 6, 1978

[51] Int. Cl.$^3$ .................... C09K 3/00; G01N 29/04
[52] U.S. Cl. ........................ 73/644; 73/104; 252/301.19; 252/316; 252/408.1; 252/DIG. 1; 252/600; 436/5
[58] Field of Search ............ 73/620, 622, 627, 629, 73/632, 639, 644; 252/316, 408, 301.19

[56] References Cited

U.S. PATENT DOCUMENTS

| | | | |
|---|---|---|---|
| 3,304,262 | 2/1967 | Corey | 252/316 X |
| 3,367,872 | 2/1968 | Martinek et al. | 252/316 X |
| 3,621,709 | 11/1971 | Frey | 73/644 |
| 3,740,421 | 6/1973 | Schmolka | 252/316 X |
| 3,826,127 | 7/1974 | Molina | 73/644 X |

OTHER PUBLICATIONS

"Cab-0-Sil", Cabot Corp., 1968, pp. 8–10.

*Primary Examiner*—Richard D. Lovering
*Attorney, Agent, or Firm*—Charles T. Silberberg; Max Geldin

[57] ABSTRACT

Substantially non-pollutant and non-toxic water washable composition in the form of a gel for use in nondestructive ultrasonic inspection of surface and subsurface flaws and discontinuities in bodies comprising a (1) poly(oxypropylene) poly(oxyethylene) condensate having a molecular weight ranging from about 1,000 to about 15,000, and (2) silica, particularly fumed silica, such silica being present in certain proportions, e.g. about 5% by weight of the composition. The composition or gel is applied to a surface of a body such as a metal aircraft structural part, and a probe or transducer of an ultrasonic testing device is contacted or pressed against the gel, and the transducer is caused to move or slide in various directions on the gel to transmit ultrasonic energy through the gel and the object, to inspect the object and locate any surface or subsurface flaws or discontinuities.

29 Claims, No Drawings

ULTRASONIC COUPLANT GEL COMPOSITIONS AND METHOD FOR EMPLOYING SAME

BACKGROUND OF THE INVENTION

This invention relates to the inspection of surface and subsurface flaws and discontinuities in objects by ultrasonic nondestructive testing, and is particularly concerned with the provision of a novel improved ultrasonic couplant composition having a minimum of components to provide good ultrasonic transmission and particularly adapted for use for such ultrasonic inspection, such composition being substantially non-polluting and having a low degree of toxicity and corrosion; and also to a method of ultrasonic inspection employing such novel composition.

Ultrasonic nondestructive testing of bodies such as metal parts has been developed. This is a method which utilizes UHF (ultra-high frequency) sound waves to detect discontinuities in parts. An ultrasonic testing device is employed, in which a probe or transducer is placed in contact with a surface of the part to be inspected. Ultrasonic waves are generated by applying a pulsed oscillating voltage from a pulser to a transducer (piezoelectric crystal). When the transducer is electrically excited and is adequately coupled to a part being inspected, an ultrasonic wave passes into the part. A change in acoustic properties of the part (surface and subsurface cracks, discontinuities, part surfaces, interfaces) reflects the wave back to the transducer. The reflected wave mechanically stresses the transducer and the transducer generates electrical charges. The electrical signals are applied to an amplifier circuit with the ultrasonic instrument, where they are amplified and displayed on a CRT (cathode-ray tube).

In the above procedure, a couplant is required to be applied to a surface of the object to be tested, to provide an effective medium for ultrasonic transmission between the transducer or probe applied to the surface of the body, and the body undergoing nondestructive testing. Thus, the primary purpose of couplants is to provide a suitable ultrasonic path between the transducer and part being inspected. Air is a poor conductor of ultasonic energy. The couplant also fills in and smooths out irregularities of a part's surface and aids in movement of the transducer. A further purpose of the couplant is to serve as an acoustic impedance matching medium. The closer the couplant acoustic impedance matches that of the part being inspected, the better the ultrasonic wave transfer.

Ultrasonic coupling compositions which have been employed to date by the industry include for example, water, glycerin, light oil and petroleum jelly or grease. These materials have been used in the past basically because of their relatively good ultrasonic transmission characteristics. However, none of the prior art couplants such as those noted above have all of the desirable features required for efficient ultrasonic inspection of parts. Thus, for example, water and glycerin are corrosive to certain metals. Oils and greases usually contaminate the surface of the parts to be tested, making it necessary to degrease the parts after testing. Further, in those cases where the parts comprise titanium or its alloys, and degreasing is required, the use of highly flammable solvents which are hazardous, is necessary for this purpose, since the usually chlorinated solvents employed for degreasing are detrimental to titanium and cannot be employed. Also, certain commercially available gelled couplants are unstable and tend to dry up, leaving powdery residues. The odor level of certain prior art couplants also is undesirable.

In my U.S. Pat. No. 3,826,127 there is disclosed an improved ultrasonic couplant composition in the form of an aqueous gel containing N-methyl-2-pyrrolidone, a water soluble surfactant, e.g. a nonyl phenyl ether of polyethylene glycol, and silica. In my copending application Ser. No. 604,407, filed Aug. 13, 1975, now U.S. Pat. No. 4,269,068, issued May 26, 1981, is disclosed a heat resistant biodegradable composition for ultrasonic inspection of surfaces in the form of a gel consisting of certain aliphatic oxyalkylated alcohols and silica. Although both of the above couplant compositions have proved successful, certain toxicological problems have developed in the use of such compositions, particularly when discarded into waterways.

It is accordingly an object of the present invention to provide an ultrasonic couplant composition, that is a composition for use in ultrasonic inspection of parts, having excellent ultrasonic transmission, which is non-corrosive to metals, particularly titanium, aluminum and steel, and their various alloys, and is nonflammable and odorless, such couplant composition being easily removable from the part surface such as by washing with water, and being relatively inexpensive to manufacture.

Another important object of the present invention is the provision of a substantially non-toxic ultrasonic couplant composition, that is non-toxic to humans and to aquatic life in waterways, and which is a simple formulation and which does not require the use of mixtures of conventional solvents and wetting agents, and which is formed of an essentially single or sole vehicle in the form of a non-toxic nonionic surfactant, and which uniquely is neither bactericidal nor bacteriostatic.

A still further object is the provision of procedure employing such novel substantially non-toxic ultrasonic couplant composition for inspection of cracks, flaws and metallurgical conditions in structural components.

DESCRIPTION OF THE INVENTION

According to the present invention, it has been found that the above objects and advantages can be accomplished and a stable ultrasonic couplant, which is essentially non-toxic, is provided by employing as an essential component of such couplant, a substantially non-toxic surfactant, preferably in liquid form, comprised of certain poly(oxypropylene) poly(oxyethylene) condensates or block copolymers. A gelled ultrasonic couplant utilizing such surfactant can be produced by incorporating silica (silicon dioxide), preferably in powdered form, as gelling agent, in such surfactant. Upon incorporation of the powdered silica into the above-noted nonionic surfactant, the resulting composition is essentially in the form of a gel which can range in consistency from thin gels of relatively low viscosity to thick gels or paste having high viscosity, depending particularly upon the proportion of silica incorporated.

The resulting ultrasonic couplant compositions or gels of the invention containing the above condensate as vehicle are substantially non-toxic and are not dangerous to aquatic life if discarded in waterways, and can be handled by personnel without any significant skin or eye irritation. In addition, the couplant compositions hereof are substantially non-corrosive towards metals such as aluminum, titanium and steel. Moreover, the couplant compositions of the invention embodying the above poly(oxypropylene) poly(oxyethylene) condensate as vehicle have low flammability and a high flash point, and do not dry up.

If desired, certain additives such as alcohols or amines can be added to the mixture of the above surfactant and silica to facilitate gel formation.

Also, a small amount of a dye such as a white light visible dye or a black light visible, i.e. fluorescent, dye can be incorporated into the gel composition to function as a tracer for inspection to determine if there is any remaining residue of gel couplant on the surface of a part after removal of the couplant as by washing, from the part surface.

The essential vehicle or carrier of the ultrasonic couplant composition of the invention are closely related block copolymers in the form of poly(oxypropylene) poly(oxyethylene) condensates or surfactants having a molecular weight ranging from about 1,000 to about 15,000, preferably from about 1,000 to about 5,000. They are formed by the condensation of propylene oxide onto a propylene glycol nucleus to form a poly(oxypropylene) base, followed by the condensation of ethylene oxide onto both ends of such base. Thus, the surfactant is prepared by the controlled addition of propylene oxide to the two hydroxyl groups of a propylene glycol nucleus, followed by addition of ethylene oxide to sandwich the hydrophobe base between poly(oxyethylene) groups. The poly(oxyethylene) hydrophilic groups on the ends of the hydrophobic poly(oxypropylene) base are controlled in length to constitute from about 10% to about 80% of the final molecule.

The poly(oxypropylene) poly(oxyethylene) condensates employed in the couplant compositions of the invention can be represented by the formula:

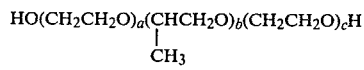

In the above formula a and c represent the number of ethylene oxide blocks at each end of the molecule, and are approximately equal, and b represents the number of propylene oxide blocks in the molecule, such that the resulting condensates have the above noted molecular weight ranging from about 1,000 to about 15,000. Thus, a and c each can range from about 2 to 130, and b can range from about 15 to 70. Accordingly, the hydrophobic and hydrophilic ratio in the molecule can be varied in controlled amounts to obtain the desired properties of the surfactant. Blends or mixtures of such condensates or block copolymus can be employed to obtain the desired balance between hydrophobic and hydrophilic groups.

These materials are nonionic surfactants of very low toxicity, that is they are virtually non-toxic and non-drying, and have low irritation to the skin. They are substantially non-pollutant to aquatic life, are substantially non-corrosive to metals, and are of low flammability, having a high flash point of the order of about 450° F. and higher.

Poly(oxypropylene) poly(oxyethylene) condensates as defined above are marketed as "Pluronic polyols" by BASF Wyandotte Corp. of Wyandotte, Mich. As previously noted, the preferred poly(oxypropylene) poly(oxyethlene) condensates for use in the couplant composition of the invention are the low molecular weight liquid surfactants of the above formula having a molecular weight ranging from about 1,000 to about 5,000, wherein a and c are substantially equal and each ranges from about 2 to 20, and b ranges from about 15 to 70. Representative surfactants of the latter type are the "Pluronic Polyols" L-44, L-62 and L-64, the "Pluronic polyol" L-64 being considered the best for the preparation of couplant gels according to the invention. The molecular weights and number of ethylene oxide and propylene oxide groups in the above specific liquid "Pluronic polyols", as well as other suitable surfactants of this type, are set forth in the Table below:

TABLE I

| Pluronic Surfactant | Average Mol. Wt. | Molecular Blocks Average Values (in Moles) | | |
|---|---|---|---|---|
| | | E.O. (a) | P.O. (b) | E.O. (c) |
| (1) L-44 | 2200 | 11 | 21 | 11 |
| (2) L-62 | 2500 | 8 | 30 | 8 |
| (3) L-64 | 2900 | 13 | 30 | 13 |
| (4) L-42 | 1630 | 5 | 21 | 5 |
| (5) L-92 | 3650 | 10 | 47 | 10 |
| (6) L-121 | 4400 | 6 | 67 | 6 |
| (7) L-122 | 5000 | 13 | 67 | 13 |

E.O. = ethylene oxide
P.O. = propylene oxide

From the above table it is seen that for the preferred Pluronic surfactants (1), (2) and (3), a and c in the above general formula each ranges from 8 to 13, and b in the above general formula ranges from 21 to 30.

Surfactants within the above general formula and having a molecular weight above about 5,000, and up to about 15,000 range from a paste to a solid. When such surfactants of higher molecular weight in the form of a paste or powder are employed, it is necessary to add water to the paste or powder to place it in liquid form, prior to incorporation of the silica. Aqueous solutions of such higher molecular weight poly(oxypropylene) poly(oxyethylene) condensates are less preferred since the presence of water in such compositions reduces the corrosion resistance thereof, and also, upon evaporation of water from such aqueous solutions the resulting composition tends to become unstable.

In addition to having the above noted low order of toxicity, and little corrosive action on metals, the above surfactants, particularly the liquid surfactants having a molecular weight ranging from 1,000 to 5,000, have good gel-forming characteristics in conjunction with silica, and provide an inexpensive ultrasonic coupler.

Although the "Pluronic polyols" themselves are practically inert toward breakdown by micro-organisms, they have an extremely low order of toxicity and are neither bactericidal or bacteriostatic, and hence can be discarded in waterways without killing fish and aquatic life. These are unique and significant characteristics not possessed generally by the ultrasonic couplant gel and the liquid vehicles thereof of the prior art, including the pyrrolidone vehicle of the couplant gel of my above patent and the aliphatic oxyalkylated alcohols of the couplant of my above co-pending application.

The poly(oxypropylene) poly(oxyethylene) condensate surfactants employed as essential component of the ultrasonic gel couplant of the present invention have high water solubility, and are more soluble in cold water than in hot water. The "Pluronic polyols" are effective thickening agents. Thus, when diluted with water or aqueous solutions, concentrated solutions of certain of such surfactants become more viscous, moving toward their gel point. The resulting viscous or thickened aqueous solutions can themselves be employed as non-toxic ultrasonic gel couplant compositions. At constant temperature and concentration, viscosity of such compositions increases with an increase in either the percent hydrophile or the molecular weight of the hydrophobe. Thus, for example, certain of the liquid "Pluronic polyols", particularly those of higher molecular weight and viscosity, such as the "Pluronic polyols" L-62, L-64, L-92, L-121 and L-122, can be employed as couplant compositions according to the invention, without addition of silica.

However, gels having the desired viscosity for use as ultrasonic contact gel couplants according to the invention, and which are stable, are more readily and rapidly produced by incorporation of silica into the poly(oxypropylene) poly(oxyethylene) condensate surfactants, according to the invention. Thus, for example when the "Pluronic polyols" L-44, L-62 and L-64 were each mixed with certain amounts of silica, a gel of the desired viscosity was readily obtained. The resultant gels were of excellent consistency and lubricity, and had excellent water removable characteristics, even superior to the couplant gels of my above patent and copending application.

The silica incorporated in the ultrasonic couplant composition is preferably in fine powder form and of particle size ranging from about 0.007 to about 0.050 micron (about 70 to about 500 Angstroms), and is an extremely fluffy, snow-white powder of extremely low bulk density. A commercially available form of this component is marketed as Cab-O-Sil M-5 by Cabot Corporation. The Cab-O-Sil has an enormous external area, one gram of Cab-O-Sil M-5 having about 400 square meters of surface area. Cab-O-Sil M-5 is a submicroscopic fire-dry fumed silica different in structure from precipitated silicas of silica gels, with a maximum density of 2.3 lbs./cu. ft.

The silica thus incorporated into the couplant composition hereof functions when uniformly dispersed in the nonionic surfactant liquid vehicle, to form a colloid dispersion in the gel which provides gel strength and physical integrity.

By addition of the silica, the consistency of the liquid vehicle or poly(oxypropylene) poly(oxyethylene) condensate surfactant changes to a gel-like appearance, with the silica additive holding the liquid vehicle in the location where it is applied, preventing the tendency of the liquid to drip or flow over a vertical or slanted surface.

The amount of silica added to the nonionic liquid surfactant can vary widely; the amount employed being sufficient to convert the nonionic surfactant liquid vehicle into a gel. Generally, however, the surfactant is present in major proportion. The amount of silica employed can range from about 2 to about 25%, preferably about 5 to about 20%, by weight of the composition. When smaller proportions of silica are employed within the above noted ranges, the resulting gels can have a thin consistency, and when larger proportions of silica are employed within the above noted ranges, the resulting gels can have a heavy or thick consistency, such as a paste. The gels produced according to the invention are generally clear and transparent or translucent. This is an important feature since after application of the gel to a part surface one can see the surface of the part through the gel. Regardless of the consistency of such gels, it has been found that they are sufficiently adhesive to prevent runoff of the couplant composition when applied to slanted or vertical surfaces, and hold the ultrasonic transducer without assistance from the operator.

It was an unexpected and unique finding that the nonionic surfactants described above can be gelled by adding the silica, since generally silica does not gel many liquids unless some other liquid such as water or solvents are present. Thus, in the couplant of my above patent containing N-methyl pyrrolidone, water is added to form the aqueous gel matrix.

Additives can be incorporated into the poly(oxpropylene) poly(oxyethylene) condensate vehicles, together with silica. These additives act as "bridging" agents which form additional links between the silica chains. Examples of such additives or bridging agents which can be employed, include alcohols such as ethylene glycols, glycerol, polyether alcohols, esters, particularly long chain esters, amides such as ethoxylated amides, amines such as long chain diamines and morpholine, and quaternary ammonium salts. Such additives function to facilitate gel formation and mixing of the silica with the surfactant hereof, and certain of the additives such as morpholine, also being a corrosion inhibiting material and aiding in resisting corrosion of metals by the ultrasonic couplant composition of the invention. The amount of such additives which can be employed can range from about 0.1 to about 5%, usually about 1 to about 4%, by weight of the composition.

It is to be understood that such additives are optional and need not be employed in the couplant composition of the invention.

It is often desirable to be able to check the part surface for the presence of residual gel, after inspection of the part has been completed and the bulk or major portion of the gel has been removed from the surface, as by a water wash. This can be accomplished by incorporating either a daylight visible dye or a fluorescent dye into the gel or couplant composition of the invention, and viewing the surface of the part under proper lighting conditions to detect any traces of the gel as indicated by the presence of colored or fluorescent residues imparted by the presence of the dye in the composition. For this purpose, it is preferred to incorporate as an optional component a fluorescent dye which is either colorless or only lightly colored when viewed by visible light, but which provides a bright fluorescent color when viewed under fluorescent or "black" light. Thus the presence of the dye in the gel still renders the gel clear in white or ordinary daylight so that the part surface can be viewed through the layer of gel applied to the part surface.

Various types of fluorescent dyes can be employed including for example the dye marketed as Fluorol 7GA and Morton Fluorescent Yellow G, as well as other fluorescent dyes such as those marketed as Calcofluor Yellow, Axosol Brilliant Yellow 6GF, Rhodanine B, Rhodanine 6GDN, Calcofluor White RW, Blancophor White AW, Auramine and Eosine G. The abovenoted Rhodanine dyes, Auramine and Eosine G fluoresce in a color range from greenish yellow to red. There can also be employed non-fluorescent or daylight type dyes such as azo type dyes, e.g. xyleneazo-beta-naphthol, Mefford No. 322 dye, believed to be o-tolueneazoxyleneazo-beta-naphthol, and the azo dyes marketed as Oil Red "O" and Sudan Red. These dyes can be employed where daylight or white light is only available. Here also it is preferred to employ those daylight dyes which are light colored and which permit the gel to be sufficiently transparent to permit viewing the surface of the part to which the gel is applied, through the gel layer or film.

The amount of the optional dye component, e.g. fluorescent or daylight dye, employed, can vary, but it is generally employed in a small amount ranging from about 0.1 to about 5%, preferably about 0.2 to about 2%, by weight of the composition.

Illustrative examples of ultrasonic couplant compositions according to the invention, but not in limitation thereof, are set forth in the table below, the amounts of the respective components being expressed in terms of percent by weight.

| | Couplant Compositions Examples (% by weight) | | | |
|---|---|---|---|---|
| Name of Material | 1 Thin | 2 Medium | 3 Thick | 4 Extra Thick |
| Pluronic Polyol L-62 (liquid) | 95 | 90 | 85 | 80 |
| Cab—O—Sil M-5 (fumed silica) | 5 | 10 | 15 | 20 |

The thin couplant gels such as Example 1 of the table above, can have a viscosity of up to about 10,000 cps, and the medium to thick couplant gels, as represented by Examples 2 and 3 of the above table, can have a viscosity ranging from about 25,000 to 60,000 cps or higher. Extra thick couplant gels in the form of a heavy paste as represented by Example 4 above, have substantially higher viscosity.

The components of the couplant gel composition of the invention can be mixed together employing high shear mixing under vacuum, to facilitate uniform mixing and rapid gel formation.

In employing the ultrasonic couplant composition or gel according to the invention, for purposes of ultrasonic inspection of a part, the part employed, if necessary, can first be cleaned to remove any contaminants from the part surface. The ultrasonic couplant gel of the invention is readily applied over the surface area of the part to be inspected by ultrasonic transmission through the part. For this purpose the gel can be dispensed and applied to the part surface to provide a thin layer of couplant, by any suitable means such as by the hand, spatula or brush. The probe or transducer of the ultrasonic test equipment is then pressed into contact with the gel on the surface of the part, and is readily moved as by sliding over the gelled surface in any direction necessary for inspection of cracks, flaws, or discontinuities such as part surfaces or interfaces, which may be contained on the surface of the part or within the part. The ultrasonic system for this purpose includes means in the form of a probe or transducer to generate ultrasonic energy, a couplant according to the present invention, and an ultrasonic instrument. The latter instrument contains suitable circuits, including a receiver-amplifier circuit and a CRT for displaying electrical signals generated by the transducer when discontinuity echoes are present, corresponding to any flaws, cracks or discontinuities in the body, as the transducer is moved over the gel on the surface of the body.

The sensitivity of the ultrasonic equipment employed should be such as to be capable of detecting the smallest defect which may be encountered in the part being tested. The thin layer or film of ultrasonic couplant gel of the invention formed on the surface of the part between the probe or transducer and the part surface maintains excellent ultrasonic transmission between the transducer and the part at all times. The presence of cracks, flaws or discontinuities on the surface or within the body of the part being tested is detected by variations in noise signals received by the testing unit, and which can be indicated on the CRT display mechanism. If there is improper coupling between the transducer and the body being tested, there will be an absence of noise signals received by the test unit. By means of the ultrasonic testing equipment employed, in conjunction with the thin film of gel couplant according to the invention, on the surface of the body, the size of flaws, cracks or discontinuities on or in the test body, for example the length thereof as well as their orientation, can be detected.

The above described ultrasonic test system and equipment is well known and since it forms no part of the present invention it is not described in detail herein.

After the ultrasonic inspection is completed, the layer or film of couplant composition or gel can be removed readily from the surface of the part by the application of water thereto, as by a water spray, or sprayed mixture of air and water, and the mixture so removed can be discharged to the sewer and into waterways due to the substantially non-toxic nature particularly of the poly-(oxypropylene) poly(oxyethylene) condensate vehicle thereof. Alternatively, such gel layer can be wiped clean from the surface of the part with dry cloths followed by a water moistened wiping. Where the ultrasonic couplant composition or gel of the invention contains an optional fluorescent dye component, the surface area of the part from which the gel layer has been removed can be viewed under fluorescent or "black" light illumination to check for the presence of residual or trace amounts of the gel. Any such traces or residual gel will provide bright fluorescent indications, so that a final removal operation of the residual gel can then be performed in those specific areas in which the gel still remains. As previously noted, such excess or residual gel can be removed by water spraying since the gel is highly soluble in water.

Alternatively, in place of employing a fluorescent dye, a dye such as an azo dye which is visible by ordinary white light or daylight can be employed and any residual gel indicated by any dye smears under ordinary visible light, can then be removed from the part surface in the manner noted above.

As previously indicated, the components of the ultrasonic couplant composition or gel of the invention can be varied, and the amounts thereof varied as described above to provide a formulation which has the desired viscosity for the particular purpose. Preferably, the viscosity of the gel is such that it can be readily applied by means noted above over the part surface to form a thin film or layer of the gel on the surface, and the ultrasonic transducer or probe can be readily moved or can readily slide on the gel surface from one selected area to another. It is particularly noteworthy that in addition to its ability to be readily applied, the ultrasonic couplant gel composition of the invention, due to its viscosity, can be employed on vertical and overhead surface applications without dripping of the composition, and the ultrasonic probe or transducer remains adhered to the geltreated surface in horizontal, vertical and overhead surface applications, permitting the operator freedom of both hands for example to return to the ultrasonic console of the test equipment and make adjustments, when necessary.

The couplant composition or gel of the invention can be employed for ultrasonic nondestructive testing of all types of parts, particularly metal parts of aircraft such as titanium and aluminum wing skins, structural hardware such as bulkheads or wing spars of aircraft, and aluminum, steel or titanium castings. Such ultrasonic testing process employing the couplant composition of the invention can be used to detect so-called "unbonds", e.g. of a fusion welded airplane fuselage bulkhead. Thus the ultrasonic couplant composition of the invention can be employed to detect surface and subsurface flaws and discontinuities, for example cracks, voids and unbonds in the fusion welding to determine the nature and integrity of the welds.

The following are examples of practice of the invention employing the novel ultrasonic coupling composition hereof.

EXAMPLE 5

The composition of Example 1 above in the form of a thin gel was applied by brushing to selected areas of aluminum parts to form a thin layer of the gel on the part surface. The transducer of an ultrasonic test equipment was pressed into contact with the surface of the gel on the respective parts and was moved by sliding in various selected directions over the gel along the surface of the parts. Variations in noise signals on the CRT display unit of the test equipment indicated cracks and discontinuities in the part, and presenting an indication of the location, orientation and size of very small as well as large cracks and flaws in the part.

After testing was completed, the gel layer was removed readily from the parts by an air-water spray, the compositions so removed being substantially non-toxic and sewered.

EXAMPLE 6

To the couplant gel composition of Example 1 is added 3% ethylene glycol, or morpholine, or glycerol, by weight.

The resulting compositions permit easier mixing of the components, and result in more rapid gellation than in the absence of the above additives.

The resulting compositions provide excellent ultrasonic couplant gels for use following the procedure of Example 5, and are readily washable from the part surface following ultrasonic inspection of the part surface for cracks and flaws.

EXAMPLE 7

To the ultrasonic couplant composition of Example 5, was added 0.5% of Morton Fluorescent Yellow G dye by weight of the composition.

The resulting couplant gel was applied to a part surface and a transducer of an ultrasonic test equipment was pressed into contact with the surface of the gel and moved thereover to detect variations in noise signals and thereby to detect cracks and flaws in the part surface.

The gel containing the fluorescent dye of this example had a light yellow coloration but was transparent and the part surface could be viewed through the gel layer.

After testing was completed, the gel layer was removed from the part by an air-water spray, the composition so removed was substantially non-toxic and sewered. The area from which the gel layer was removed was then viewed under fluorescent or black light, and residual gel on the surface was indicated by very bright fluorescent yellow smears. Such residual gel was then removed by a final water spray.

EXAMPLE 8

The procedure of Example 5 was substantially repeated but employing the more viscous couplant gel composition of Example 2 above.

Particular care was taken to remove practically all of the gel following ultrasonic inspection by an air-spray, leaving essentially no residual gel on the surface of the part.

Results similar to Example 5 were obtained.

EXAMPLE 9

The procedure of Example 5 is substantially repeated employing the relatively viscous liquid "Pluronic polyol" surfactant L-122, having a molecular weight of 5,000 as couplant gel without any addition of silica thereto.

Although such gel functions satisfactorily as an ultrasonic couplant gel, it does not have the holding power, particularly on slanted and vertical surfaces, of the couplant gel of Example 5, which contains silica, and is not as stable as the couplant gel of Example 5.

From the foregoing, it is seen that the invention provides a highly effective substantially non-toxic water washable and substantially non-corrosive ultrasonic couplant composition in the form of a gel which is non-flammable, and which can be applied effectively to parts positioned at various angles, without runoff or dipping, and which can be readily removed from a part surface by simply washing. The couplant gels of the invention contain as an essential component, a vehicle in the form of certain poly(oxypropylene) poly(oxyethylene) condensates, and preferably incorporating therein silica, particularly fumed silica. Such poly(oxypropylene) poly(oxyethylene) condensates are compatible with metals, are substantially non-volatile, non-toxic, non-pollutant, and have high flash points of the order of 450° F. and higher.

While I have described particular embodiments of my invention for the purpose of illustration within the spirit of the invention, it will be understood that the invention is not to be taken as limited except by the scope of the appended claims.

I claim:

1. A method for detecting surface and subsurface flaws and discontinuities in an object, which comprises applying to a surface of said object a water washable substantially non-toxic ultrasonic couplant gel composition which consists essentially of a nonionic surfactant in the form of a poly(oxypropylene) poly(oxyethylene) condensate having a molecular weight ranging from about 1,000 to about 15,000, and an amount of silica sufficient to convert said surfactant into a gel, contacting a transducer of an ultrasonic testing device with said gel on said surface of said object, and transmitting ultrasonic energy through said gel and into said object to inspect said object and locate any surface or subsurface flaws, cracks or discontinuities in said object, and removing said ultrasonic couplant composition from said surface.

2. The method as defined in claim 1, said condensate being a block coplymer having the formula:

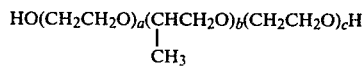

wherein a and c are approximately equal, and each can range from about 2 to 130, and b can range from about 15 to 70.

3. The method as defined in claim 2, said silica being present in an amount ranging from about 2 to about 25% by weight of said composition.

4. The method as defined in claim 2, said composition containing a fluorescent dye, and following removal from said object, inspecting said surface of said object under fluorescent light to detect any residual trace of said composition on said surface as indicated by fluorescent emission from said fluorescent dye in said composition.

5. The method as defined in claim 2, wherein said condensate is a liquid, and the molecular weight of said condensate ranges from about 1,000 to about 5,000, and wherein a and c each range from about 2 to 20, and b ranges from about 15 to 70.

6. The method as defined in claim 5, said silica being present in an amount ranging from about 2 to about 25% by weight of said composition.

7. The method as defined in claim 5, said composition also including an additive in the form of a bridging agent for said silica, said additive selected from the group consisting of alcohols, esters, amides, amines and quaternary ammonium salts.

8. The method as defined in claim 5, wherein a and c each range from 8 to 13 and b ranges from 21 to 30.

9. The method as defined in claim 8, wherein said silica is present in an amount ranging from about 5 to about 20% by weight of said composition.

10. The method as defined in claim 9, said composition also including a fluorescent dye in an amount of about 0.1 to about 5% by weight, and said silica is fumed silica, said composition ranging from a thin to a heavy consistency, and following removal of said composition from said object, inspecting said surface of said object under fluorescent light to detect any residual trace of said composition on said surface as indicated by fluorescent emission from said fluorescent dye in said composition.

11. The method as defined in claim 1, said silica being present in an amount ranging from about 2 to about 25% by weight of said composition.

12. The method as defined in claim 1, said composition containing a dye, and following removal of said composition from said object, inspecting said surface of said object under suitable light to detect any residual trace of said composition on said surface as indicated by light emission from said dye in said composition.

13. The method as defined in claim 1, said composition also including an additive in the form of a bridging agent for said silica, said bridging agent forming additional links between the silica chains.

14. The method as defined in claim 13, said additive selected from the group consisting of alcohols, esters, amides, amines and quaternary ammonium salts.

15. An essentially non-toxic composition for ultrasonic inspection of surface and subsurface flaws and discontinuities in an object, in the form of a gel consisting essentially of a nonionic surfactant in the form of a poly(oxypropylene) poly(oxyethylene) condensate having a molecular weight range from about 1,000 to about 15,000, and an amount of silica sufficient to convert said surfactant into a gel.

16. The ultrasonic couplant composition as defined in claim 15, said condensate being a block coplymer having the formula:

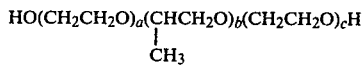

wherein a and c are approximately equal, and each can range from about 2 to about 130, and b can range from about 15 to 70.

17. The ultrasonic couplant composition as defined in claim 16, wherein said condensate is a liquid and the molecular weight of said condensate ranges from about 1,000 to about 5,000, and wherein a and c each ranges from about 2 to 20, and b ranges from about 15 to 70.

18. The ultrasonic couplant composition as defined in claim 17, wherein said silica is present in an amount ranging from about 2 to about 25% by weight of said composition.

19. The ultrasonic couplant composition as defined in claim 18, including a dye in an amount of about 0.1 to about 5% by weight of said composition.

20. The ultrasonic couplant composition as defined in claim 19, said dye being a fluorescent dye.

21. The ultrasonic couplant composition as defined in claim 21, said composition also including an additive in the form of a bridging agent for said silica, said additive selected from the group consisting of alcohols, esters, amides, amines and quaternary ammonium salts, said additive being present in an amount ranging from about 0.1 to about 5% by weight of said composition.

22. The ultrasonic couplant composition as defined in claim 21, wherein a and c each ranges from 8 to 13, and b ranges from 20 to 30, and wherein said silica is present in an amount ranging from about 5 to about 20% by weight of said composition, said gel composition ranging from a thin to a heavy consistency.

23. The ultrasonic couplant composition as defined in claim 22, wherein said silica is fumed silica.

24. The ultrasonic couplant composition as defined in claim 17, wherein a and c each ranges from 8 to 13, and b ranges from 21 to 30.

25. The ultrasonic couplant composition as defined in claim 15, said silica being present in an amount ranging from about 2 to about 25% by weight of said composition.

26. The ultrasonic couplant composition as defined in claim 15, including a small amount of a dye.

27. The ultrasonic couplant composition as defined in claim 15, said composition also including an additive in the form of a bridging agent for said silica, said bridging agent forming additional links between the silica chains.

28. The ultrasonic couplant composition as defined in claim 27, said additive also being a corrosion inhibiting material.

29. The ultrasonic couplant composition as defined in claim 27, said additive selected from the group consisting of alcohols, esters, amides, amines and quaternary ammonium salts.

* * * * *